United States Patent [19]

Cavazza et al.

[11] 4,405,638
[45] Sep. 20, 1983

[54] 2-METHOXYPHENYL ESTERS OF N-SUBSTITUTED AMINO ACIDS, A PROCESS FOR THEIR PREPARATION AND PHARMACEUTICAL COMPOSITIONS CONTAINING THEM

[75] Inventors: Claudio Cavazza; Massimo Carloni; Maria T. Ramacci, all of Rome, Italy

[73] Assignee: Sigma-Tau Industrie Farmaceutiche Riunite S.p.A, Rome, Italy

[21] Appl. No.: 372,985

[22] Filed: Apr. 29, 1982

[30] Foreign Application Priority Data

May 11, 1981 [IT]  Italy ................................ 21620 A/81
May 15, 1981 [IT]  Italy ................................ 48485 A/81

[51] Int. Cl.[3] ...................... A61K 31/38; A61K 31/22; C07C 69/00; C07D 333/16

[52] U.S. Cl. .................................. 424/275; 424/311; 549/71; 549/72; 560/144
[58] Field of Search .................. 424/278, 311; 549/71, 549/72; 560/144

[56] References Cited

U.S. PATENT DOCUMENTS 4,108,886  8/1978  Ondetti ........................... 260/455 R
4,279,842 11/1981  Cavazza .............................. 560/144

Primary Examiner—Alan Siegel
Attorney, Agent, or Firm—Bucknam and Archer

[57] ABSTRACT

The invention provides 2-methoxyphenyl esters of N-substituted amino acids, which have mucolytic, antitussive and antiinflammatory activity.

16 Claims, No Drawings

2-METHOXYPHENYL ESTERS OF N-SUBSTITUTED AMINO ACIDS, A PROCESS FOR THEIR PREPARATION AND PHARMACEUTICAL COMPOSITIONS CONTAINING THEM

DESCRIPTION OF THE INVENTION

The present invention concerns a new class of guaiacyl(2-methoxyphenyl)esters with N-substituted amino acids, a process for their preparation, their use as therapeutic agents, and pharmaceutical compositions containing them.

More particularly, the invention concerns 2-methoxyphenyl esters of the formula I:

$$\begin{array}{c} R-CH-CO-O \\ | \\ R'-CO-NH \end{array} \text{—Ar(OCH}_3\text{)} \quad (I)$$

in which:
R is hydrogen, —CH$_3$ or —CH$_2$SR'', wherein R'' represents hydrogen, —COCH$_3$ or —CH$_2$COOH;
R' is —CH$_3$ or $$\begin{array}{c} \text{thienyl}-CO-S-CH- \\ | \\ CH_3 \end{array}$$

More particularly, the invention concerns the 2-methoxyphenyl esters of the following N-substituted amino acids: (1) N-acetlyglycine; (2) N-[2-(2-thenoylthio)propionyl]glycine; (3) N-acetylalanine; (4) N-[2-(2-thenoylthio)propionyl]alanine; (5) N-acetylcysteine; (6) N,S-diacetylcysteine; (7) N-acetyl-S-carboxymethylcysteine; (8) N-[2-(2-thenoylthio)propionyl]cysteine; (9) N-[2-(2-thenoylthio)propionyl]-S-acetylcysteine; (10) N-[2-(2-thenoylthio)propionyl]-S-carboxymehtylcysteine.

2-Methoxyphenyl esters with amino acids are known, said compounds having mucolytic activity: the European Patent Application no. 79830052.1 in the Applicant's name, claims guaiacyl esters of α- and β-mercaptopropionylalanine and α- and β-mercaptopropionylglycine and the related pharmaceutical compositions containing these esters, which are endowed with high mucolytic properties (without increasing the bronchial secretion). However, some of the esters described in the mentioned European Patent Application are not very stable; consequently, the pharmaceutical formulations containing these compounds are subjected to an unpleasant smell after a relatively short-term storage, particularly in tropical countries, with obvious negative effects on the patient and on the therapeutical effectiveness of the formulations.

Another drawback of the known 2-methoxyphenyl esters lies in their low melting point (some of them are liquid at room temperature); this fact involves obvious formulations difficulties.

It has now been found that the new 2-methoxyphenyl esters of formula (I), endowed with a very good mucolytic antitussive and antiinflammatory activity, without increasing effects on the bronchial secretion, show a much higher stability than the known guaiacyl esters, and are moreover crystalline compounds whose formulation does not involves any difficulty.

It has moreover been found that, whereas the free SH group of known mercapto compounds (such as N-(2-mercaptopropionyl)glycine) can be easily oxidized in the body before reaching the action place (for instance the respiratory apparatus mucose), this is not the case of the compounds of formula I. Moreover, these compounds are characterized by a slow hydrolysis; this fact allows the transport and the utilization of the still active SH groups.

The present invention concerns also a process for the preparation of the esters of formula I, characterized by the fact that:

(a) a compound of formula II is reacted with 2-methoxyphenol III, according to the scheme:

$$\begin{array}{c} R-CH-COX \\ | \\ R'-CO-NH \end{array} + HO-Ar \longrightarrow (I)$$

$$(II) \qquad (III)$$

wherein R and R' have the above mentioned meanings, Ar is 2-methoxyphenyl, and X represents Cl, a C$_1$–C$_4$ alkoxy group, or an —O—CO—OR'' group, wherein R'' is a C$_1$–C$_4$ alkyl group, or another activating group, such as the imidazolyl-carbonyloxy group; or (b) a compound of formula IV is reacted with a compound of formula V, according to the scheme:

$$R'-COX + \begin{array}{c} R-CH-CO-O-Ar \\ | \\ NH_2 \end{array} \longrightarrow (I)$$

$$(IV) \qquad (V)$$

wherein R, R', Ar and X have the above mentioned meanings; or (c) when R' is $$\begin{array}{c} \text{thienyl}-CO-S-CH- \\ | \\ CH_3 \end{array},$$

a compound of formula VI is reacted with a compound of formula VII, according to the scheme:

$$\begin{array}{c} \text{thienyl}-COX + HS-CH-CO-NH \\ | \\ CH_3 \end{array} \begin{array}{c} R-CH-CO-O-Ar \\ | \\ \end{array} \longrightarrow (I)$$

$$(VI) \qquad (VII)$$

wherein R, Ar and X are as above mentioned; or (d) when R' is $$\begin{array}{c} \text{thienyl}-CO-S-CH- \\ | \\ CH_3 \end{array},$$

a compound of formula IX is reacted with thiophene-2-thiocarboxylic acid VIII, according to the scheme:

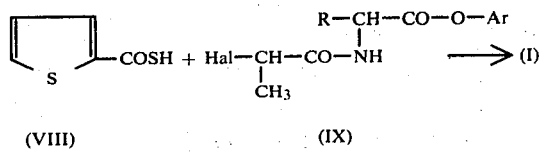

(VIII)    (IX)

wherein R and Ar are as above mentioned, whereas Hal represents chlorine, bromine or iodine.

The above schematized reactions are preferably carried out in the presence of an inorganic or organic base (for instance an alkali metal alkoxyde or hydroxyde or carbonate or hydrogen carbonate; a tertiary amine, such as triethylamine or pyridine). Alternatively, 2-methoxyphenol (III) or thiophene-2-thiocarboxylic acid (VIII) may be used in the form of their alkali metal salts, prepared before the reaction.

The reactions according to the schemes of the methods (a), (b) and (c) are generally carried out in aprotic solvents, for instance $CH_2Cl_2$, tetrahydrofuran or dioxane, at temperatures ranging from about +5° C. to about +20° C. for the first 15–60 minutes, then at room temperatures for 2–24 hours.

When X represents an —O—CO—OR" group, the corresponding mixed anhydride is generally obtained starting from ethyl chlorocarbonate.

When the reaction is carried out in a hydromiscible solvent (for instance in $CH_2Cl_2$), the solution is then washed with $H_2O$, diluted HCl and $H_2O$ until neutrality, dried and vacuum evaporated. If other solvents (THF or dioxane) are used, the reaction product is recovered by filtration of the tertiary base hydrochloride and concentration of the filtrate under vacuum. If the amino acid used as a starting compound in the schemes according to the above mentioned methods contains free SH groups, these are preliminary protected as known per se, for instance by reaction with trityl chloride or with a p-substituted benzyl halide, the S-protecting groups being later removed in conditions suited to preserve the guaiacyl ester group. Such elimination of the S-protecting group is carried out in acid medium, preferably in the presence of $CF_3$—COOH.

The reaction of thiophene-2-thiocarboxylic acid (VIII) with the halo compounds (IX) is preferably carried out in water, the acid (VIII) being employed in the form of sodium or potassium salt, obtained in situ by treatment of an aqueous solution of NaSH or KSH with 2-chlorocarbonyl-thiophene.

The process according to the invention is illustrated but not limited by the following examples.

EXAMPLE 1

To a solution of 26.9 g (0.1 moles) of 2-methoxyphenyl N-(2-thiopropionyl)aminoacetate in 120 ml of dioxane, 10.1 g (0.1 moles) of triethylamine are added. The temperature of the stirred solution is maintained between 10° and 15° C.; 14.6 g (0.1 moles) of 2-chlorocarbonylthiophene, dissolved in 30 ml of dioxane are added dropwise. After half an hour stirring, about 100 ml of dioxane are vacuum distilled and 150 ml of water are added. The precipitated oil is washed with three portions of 100 ml of $H_2O$, then cooled at 5°–10° C. for some hours. The solidified product is triturated, dried under vacuum and recrystallized with diisopropyl ether: 23.9 g (63%) of 2-methoxyphenyl N-[2-(2-thenoylthio)propionyl]aminoacetate (2) are obtained, m.p. 90.5°–92° C.

Elemental analysis: for $C_{17}H_{17}NO_5S_2$ (M.W. 379): calc.% C=53.83; H=4.48; N=3.69; S=16.89; found% C=53.61; H=4.53; N=3.54; S=16.59

IR Spectrum (nujol mull): 3340 $cm^{-1}$; 1785 $cm^{-1}$; 1665 $cm^{-1}$; 1215 $cm^{-1}$; 1185 $cm^{-1}$; 830-750-720 $cm^{-1}$.

NMR Spectrum (registered in DMSO; internal standard TMS; the chemical shifts are reported in δ): 1.56 (d, 3H, C$\underline{H}_3$—CH); 3.83 (s, 3H, OCH$_3$); 4.23 (d, 2H, NH—C$\underline{H}_2$); 4.53 (q, 1H, C$\underline{H}$—CH$_3$); 6.9–8.3 (m, 7H, arom.); 8.93 (t, 1H, N$\underline{H}$—CH$_2$)

TLC: Silica gel, toluene/diethylether 60:40; single spot.

| HPLC | column | Lichrosorb RP 18 |
|---|---|---|
|  | eluent | $H_2O$ 65 |
|  |  | $CH_3CN$ 35 |
|  |  | $CH_3COOH$ 1 |
|  | UV rivelator λ = 254 mμ | |

EXAMPLE 2

To a stirred aqueous solution of potassium thiophene-2-thiocarboxylate, prepared from 14.6 g (0.1 moles) of 2-chlorocarbonyl-thiophene and 7.92 g (0.1 moles) of KSH in 50 ml of water, 31.6 g (0.1 moles) of 2-methoxyphenyl(2-bromopropionyl)aminoacetate dissolved in 50 ml of acetone are added; the pH is adjusted at about 7.5 by addition of a 2 N KOH-solution, the temperature ranging from 25° to 30° C. When the addition is completed, stirring is continued for half an hour, the solvent is evaporated under vacuum, and the residue is dissolved in 70 ml of $CH_2Cl_2$. The organic solution is washed with water, dried on $Na_2SO_4$, and evaporated. The semisolid residue is dissolved in boiling dissopropyl ether; 26.9 g (71%) of the same compound as in Example 1 are obtained, by cooling.

EXAMPLE 3

The preparation is carried out as described in Example 2 but NaSH and NaOH are used instead of the corresponding potassium compound. 2-Methoxyphenyl N-[2-(2-thenoylthio)propionyl]aminoacetate in a yield of 67% is obtained.

EXAMPLE 4

Operating as described in Example 2, but using 2-methoxyphenyl(2-chloropropionyl)aminoacetate, the same compound in a yield of 74% is obtained.

EXAMPLE 5

A solution of 21.6 g (0.1 moles) of 2-(2-thenoylthio)-propionic acid in 80 ml of CHCl$_3$ is treated with 14.3 g (0.12 moles) of SOCl$_2$, at room temperature. After 8 hours the solvent is removed under vacuum, and the raw acyl chloride is dissolved in 50 ml of benzene. This solution is added with 18.1 g (0.1 moles) of 2-methoxyphenyl aminoacetate and 7.9 g of pyridine in 50 ml of benzene. The mixture is stirred for two hours at room temperature, and for two additional hours at 50° C. The solvent is vacuum distilled, the residue is treated with water and extracted with $CH_2Cl_2$. The solution is worked out as described in Example 2; the final product is recovered in a 55% yield, m.p. 89°–92° C.

EXAMPLE 6

A solution of 21.6 g (0.1 moles) of 2-(2-thenoilthio)-propionic acid and 10.1 g (0.1 moles) of thriethylamine in 75 ml of $CHCl_3$ is added with 10.8 g (0.1 moles) of ethyl chlorocarbonate, dissolved in 25 ml of $CHCl_3$, the temperature ranging from $-10°$ to $0°$ C. The so-prepared solution of mixed anhydride is then reacted with a solution of 18.1 g (0.1 moles) of 2-methoxyphenyl aminoacetate in 50 ml of $CHCl_3$. The mixture is kept at 0° C. for 1 hour, then at room temperature for 4 hours. The solvent is evaporated under vacuum and the residue is worked out as described in Example 2. 29.6 Grams of 2-methoxyphenyl N-[2-(2-thenoylthio)propionyl]aminoacetate are obtained, m.p. 90°-92° C.

EXAMPLE 7

A solution of 27.3 g (0.1 moles) of N-[2-(2-thenoylthio-propionyl]glycine in 250 ml of anhydrous tetrahydrofuran is added with 16.2 g (0.1 moles) of carbonyldiimidazole. The mixture is heated to 50° C. in a water bath. When the evolution of $CO_2$ is completed, 12.4 g (0.1 moles) of guaiacol and about 100 mg of sodium methoxyde are added. The temperature is kept at 50° C. for 2 hours, under stirring; the progress of the reaction is controlled by TLC. The solvent is then removed under vacuum, the raw product is washed with water and dissolved in $CH_2Cl_2$. The solution is worked out as in Example 2; 18.6 g of the same product are obtained, m.p. 90°-92° C.

EXAMPLE 8

5.4 Grams (0.02 moles) of N-[2-(2-thenoylthio)propionyl]glycine and 2.0 g (0.02 moles) of triethylamine are added to 50 ml of anhydrous $CH_2Cl_2$. The mixture is cooled at 0° C.; then a solution of 2.2 g (0.02 moles) of ethyl chlorocarbonate in 10 ml of anhydrous $CH_2Cl_2$ is added. The temperature of the mixture is then raised to 5° C., and a solution of 2.5 g (0.02 moles) of guaiacol, 2.0 g (0.02 moles) of triethylamine and 20 ml of $CH_2CH_2$ is added. Stirring is continued for 1 hour at 5° C., then for 4 hours at room temperature. The solution is washed with $H_2O$, diluted HCl, $H_2O$, then is dried on $Na_2SO_4$ and evaporated to dryness under vacuum. By crystallization from acetone/hexane, a very pure compound, identical to the product of Example 1, is obtained, m.p. 92°-93° C. The toxicological and pharmacological properties of the esters of formula I results from the below reported considerations.

ACUTE TOXICITY $LD_{50}$ of the compounds of formula (I), evaluated by the Weil method ("Tables for convenient calculation of median effective dose ($LD_{50}$ or $ED_{50}$) and instructions in their use", Biometrics, 249-253, 1952), by intraperitoneal administration in the mouse. The results are reported in Table 1.

TABLE 1

| \multicolumn{3}{l}{$LD_{50}$ and confidential limits, mg/kg i.p., of the compounds of formula I. Weil method, N = 4 K = 4} |
|---|---|---|
| Compound | $LD_{50}$ | confidential limits |
| (1) | 1010 | (960-1050) |
| (2) | 1240 | (1180-1300) |
| (3) | 1150 | (1100-1200) |
| (4) | 960 | (809-1140) |
| (5) | 1270 | (1200-1340) |
| (6) | 1580 | (1510-1650) |
| (7) | 1250 | (1180-1320) |

TABLE 1-continued

| \multicolumn{3}{l}{$LD_{50}$ and confidential limits, mg/kg i.p., of the compounds of formula I. Weil method, N = 4 K = 4} |
|---|---|---|
| Compound | $LD_{50}$ | confidential limits |
| (8) | 980 | (850-1110) |
| (9) | 1230 | (1100-1360) |
| (10) | 1340 | (1250-1430) |

EXPECTORATING ACTIVITY

The experimentation was carried out on male rabbits, weighting 2-3 kg, narcotized with ethyl urethane, according to the method described by Perry et al. (J. Pharm. Exp. Ther. 73, 65 (1941)). Each compound of formula (I) was administered to 5 rabbits in doses ranging from 20 to 40 mg, 1 hour after the incannulation. The control group (8 rabbits) was given only water. The amount of secretion was determined 1, 2 and 4 hours after the administration. The results reported in Table 2 show that the compounds (I) do not possess expectorant activity.

TABLE 2

| \multicolumn{4}{l}{Effects of compounds of formula (I) on the bronchial secretion} |
|---|---|---|---|
| | \multicolumn{3}{l}{Percentage variations ($\pm$ standard error) of the bronchial secretion, in comparison with the basic values, in the following times after the administration} |
| Compounds | 1h | 2h | 4h |
| Control ($H_2O$) | $+1 \pm 0,03$ | $+2 \pm 0,04$ | $+3,5 \pm 0,06$ |
| (1) | $+1,3 \pm 0,02$ | $-1,4 \pm 0,03$ | $+2,3 \pm 0,07$ |
| (2) | $+0,3 \pm 0,01$ | $+0,7 \pm 0,03$ | $+1,4 \pm 0,05$ |
| (3) | $+0,8 \pm 0,04$ | $+1,2 \pm 0,04$ | $+2,7 \pm 0,08$ |
| (4) | $+1,5 \pm 0,05$ | $+1,9 \pm 0,08$ | $+2,5 \pm 0,09$ |
| (5) | $+0,9 \pm 0,05$ | $+2,1 \pm 0,01$ | $+3,8 \pm 0,09$ |
| (6) | $+0,4 \pm 0,05$ | $+2,1 \pm 0,05$ | $+1,9 \pm 0,04$ |
| (7) | $+0,5 \pm 0,03$ | $+0,7 \pm 0,07$ | $+1,9 \pm 0,09$ |
| (8) | $+1,8 \pm 0,04$ | $+1,7 \pm 0,09$ | $+2,7 \pm 0,05$ |
| (9) | $+1,9 \pm 0,03$ | $+1,5 \pm 0,04$ | $+2,4 \pm 0,04$ |
| (10) | $+0,8 \pm 0,02$ | $+1,3 \pm 0,04$ | $+2,1 \pm 0,03$ |

MUCOLYTIC ACTIVITY

The mucolytic activity was tested in vitro, using the method described by Morandini et al. (Lotta contro la tubercolosi 47, no. 4 (1977)). The modifications induced by compounds of formula (I) and acetylcysteine on the rheological properties of the human secretion were followed using a thromboelastograph. The data reported in Table 3 show the better activity of the compounds (I) in comparison with acetylcysteine, in terms of reduction of the density of human secretion.

TABLE 3

| \multicolumn{3}{l}{Mucolytic activity in vitro of compounds (I) and acetylcysteine: modifications of the density of human secretion.} |
|---|---|---|
| | \multicolumn{2}{l}{Percentage decrease ($\pm$ standard error) of the curve versus the maximal amplitude (x) after addition of 1 ml of a 10% solution of the compounds, at the indicated dilutions.} |
| Compounds | 1/30 | 1/60 |
| (1) | 78 | 55 |
| (2) | 82 | 62 |
| (3) | 80 | 58 |
| (4) | 84 | 60 |
| (5) | 82 | 57 |
| (6) | 82 | 59 |
| (7) | 76 | 55 |
| (8) | 78 | 48 |

TABLE 3-continued

Mucolytic activity in vitro of compounds (I) and acetyl-cysteine: modifications of the density of human secretion.

| Compounds | Percentage decrease (± standard error) of the curve versus the maximal amplitude (x) after addition of 1 ml of a 10% solution of the compounds, at the indicated dilutions. | |
|---|---|---|
| | 1/30 | 1/60 |
| (9) | 75 | 43 |
| (10) | 74 | 41 |
| acetylcysteine | 71 | 22 |

(x) Mucolytic activity index

EFFECT ON THE CILIARY ACTIVITY

The effects of the compounds of formula (I) on the ciliary motility were examined by microscopical observation of the ciliary movement in tracheal rings of rats immersed in solutions of the compounds. This method allows to control-against concentration and time-the block of the ciliary movement induced by the tested compounds, said block being due to the removal of the mucus from the ciliate epithelium.

For compounds to be used in solution, said block must take place in a contact time at least of 15 minutes.

The compounds of formula (I), used as 2% aqueous solutions, induced the block of the ciliary activity in times ranging from 18 to 20 minutes.

BRONCHOSECRETOGOGIC ACTIVITY OF COMPOUND (2)

The bronchosecretogogic activity of compound (2), i.e. 2-methoxyphenyl N-[2-(2-thenoylthio)propionyl]aminoacetate, was tested according to the method of the sodium fluoresceine in the rat, as described by Mawatari (Experimental Studies on the expectorant action of several drugs, Kagoshima Daigaku Igaku Zasshi 27, 561 (1976)), in comparison with S-carboxymethyl-cysteine (CMC) and N-(2-mercaptopropionyl)glycine (MPG).

The results are reported in Table 4.

TABLE 4

Removal of the sodium fluoresceine from the bronchial tree (percentage increase versus the controls).

| number of animals | weight (g) ± s.e. | compound | mg/kg i.p. | % increase |
|---|---|---|---|---|
| 10 | 226 ± 2.9 | CMC | 500 | 33.4 |
| 10 | 206 ± 7.1 | (2) | 500 | 123.5 |
| 10 | 216.6 ± 4 | MPG | 500 | 21.9 |

As shown in Table 4, compound (2) is endowed with a bronchosecretogogic activity much higher than CMC and MPG, which are widely used as mucolytic agents.

ANTITUSSIVE ACTIVITY OF COMPOUND (2)

This activity was tested on Guinea pigs, in which cough was induced by citric acid aerosol, in comparison with codeine. Compound (2) was administered per os and intraperiotoneally. The results are reported in Table 5.

TABLE 5

Antitussive activity. Cough induced in Guinea pigs by citric acid aerosol.

| compound | dose mg/kg | administration | % inhibition of the cough |
|---|---|---|---|
| codeine | 25 | per os | 75.6 |
| codeine | 12.5 | i.p. | 90.2 |
| (2) | 500 | per os | 82.3 |
| (2) | 100 | i.p. | 95.8 |

PHARMACOKINETICS OF COMPOUND (2)

"In vitro" and "in vivo" tests were carried out. The "in vitro" tests showed that compound (2) is enzymetically hydrolized giving N-(2-mercaptopropionyl)glycine, thiophene-2-carboxylic acid and guaiacol. The highest esterase activity is showed by the lung.

"In vivo" studies, carried out in the rat, showed that compound (2) is mostly absorbed as such after oral administration. After administration of equimolecular doses of N-[2-(2-thenoylthio)propionyl]glycine and of the corresponding 2-methoxyphenyl ester (compound (2)), higher lung concentrations of N-(2-mercaptopropionyl)glycine and thiophene-2-carboxylic acid are found in the case of compound (2) administration. In other words, compound (2) shows a high pulmonary tropism.

This invention also concerns the therapeutic use of esters of formula (I) in the treatment of bronchial diseases, and the oral and parenteral administration to patients of a therapeutically efficient amount of an ester of formula (I).

This use comprises the administration of about 15–70 mg/kg of body weight of esters of formula (I), although lower or higher doses may be administered on the basis of age, weight, general conditions and pathology of the patient.

The pharmaceutical formulations of this invention may be in a solid or liquid form, for instance as tablets, solutions, syrups, phtials and so on. The following, non limitative examples, illustrate some formulations according to the invention.

| Phtials for aerosol or intramuscular injection | |
|---|---|
| 2-Methoxyphenyl N—[2-(2-thenoylthio)-propionyl]aminoacetate | mg 400 |
| Sodium metabisulfite | mg 10 |
| Apyrogenic distilled water | ml 3 |
| Syrup | |
| 2-Methoxyphenyl N—[2-(2-thenoylthio)-propionyl]aminoacetate | g 4 |
| 70% Sorbitol | g 15 |
| Saccharose | g 50 |
| Ethanol | ml 1 |
| Methyl 4-hydroxybenzoate | mg 0.2 |
| Distilled water | up to ml 100 |
| Suppositories | |
| 2-Methoxyphenyl N—[2-(2-thenoylthio)-propionyl]aminoacetate | mg 400 |
| Sodium metabisulfite | mg 20 |
| Excipients sufficient to make up to | |

I claim:
1. 2-methoxyphenyl esters of formula I

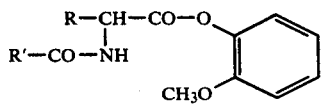

in which:

R is hydrogen, —CH₃ or —CH₂SR", wherein R" represents hydrogen, —COCH₃ or —CH₂COOH;
R' is —CH₃ or

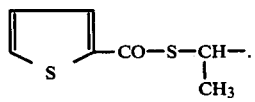

2. As a new compound according to claim 1, the 2-methoxyphenylester of N-acetylglycine.

3. As a new compound according to claim 1, the 2-methoxyphenylester of N-[2-(2-thenoylthio)propionyl]glycine.

4. As a new compound according to claim 1, the 2-methoxyphenylester of N-acetylalanine.

5. As a new compound according to claim 1, the 2-methoxyphenylester of N-[2-(2-thenoylthio)propionyl]alanine.

6. As a new compound according to claim 1, the 2-methoxyphenylester of N-acetylcysteine.

7. As a new compound according to claim 1, the 2-methoxyphenylester of N,S-diacetylcysteine.

8. As a new compound according to claim 1, the 2-methoxyphenylester of N-acetyl-S-carboxymethylcysteine.

9. As a new compound according to claim 1, the 2-methoxyphenylester of N-[2-(2-thenoylthio)propionyl]cysteine.

10. As a new compound according to claim 1, the 2-methoxyphenylester of N-[2-(2-thenoylthio)propionyl]-S-acetylcysteine.

11. As a new compound according to claim 1, the 2-methoxyphenylester of N-[2-(2-thenoylthio)propionyl]-S-carboxymethylcysteine.

12. Pharmaceutical compositions with mucolytic, bronchosecretogogic and antitussive activity, characterized by the fact that an ester of formula I

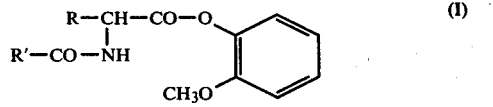

wherein R and R' are as above indicated, is contained as the active ingredient.

13. Pharmaceutical compositions according to claim 12, in the pharmaceutical dosage form of suppositoires.

14. Pharmaceutical compositions according to claim 12, in the pharmaceutical dosage form of aerosol.

15. Pharmaceutical compositions according to claim 12, in the pharmaceutical dosage form of injectable ampuls.

16. Pharmaceutical compositions according to claim 12, in the pharmaceutical dosage form of syrups.

* * * * *